United States Patent [19]

Yoon

[11] Patent Number: 4,860,746
[45] Date of Patent: Aug. 29, 1989

[54] ELASTIC SURGICAL RING CLIP AND RING LOADER

[76] Inventor: InBae Yoon, 2131 Highland Ridge Dr., Phoenix, Md. 21131

[21] Appl. No.: 63,913

[22] Filed: Jun. 19, 1987

Related U.S. Application Data

[60] Continuation-in-part of Ser. No. 789,663, Oct. 21, 1985, Pat. No. 4,794,927, which is a division of Ser. No. 370,170, Apr. 20, 1982, Pat. No. 4,548,201.

[51] Int. Cl.$^4$ ............................................. A61B 17/12
[52] U.S. Cl. ................................ 128/326; 128/303 A
[58] Field of Search ................... 128/303 A, 325-327, 128/346

[56] References Cited

U.S. PATENT DOCUMENTS

| | | | |
|---|---|---|---|
| 2,619,964 | 12/1952 | Thaete | 128/303 A |
| 4,167,188 | 9/1979 | Lay | 128/326 |
| 4,485,814 | 12/1984 | Yoon | 128/327 |
| 4,493,319 | 1/1985 | Polk et al. | 128/303 A |
| 4,548,201 | 10/1985 | Yoon | 128/303 A X |

FOREIGN PATENT DOCUMENTS

491348 8/1938 United Kingdom ................ 128/346

Primary Examiner—Dalton L. Truluck
Attorney, Agent, or Firm—Robert E. Bushnell

[57] ABSTRACT

An elastic surgical ring clip which is of a configuration to provide a ring clip having greatly increased compressive and elastic strength. The clip may be of spherical configuration and has a central lumen which may have a variety of cross-sectional configurations to increase tissue gripping. A ring loader for loading elastic rings onto the distal end of a ring applicator device including a conical ring expander and a conical ring dilator which is slipped over and pushed along the ring expander to dilate rings and place the dilated rings on a ring applicator device distal end. A kit including a ring loader and one or more elastic surgical ring clips.

17 Claims, 2 Drawing Sheets

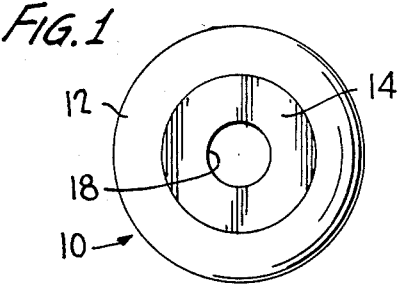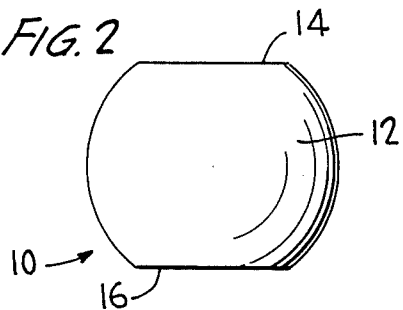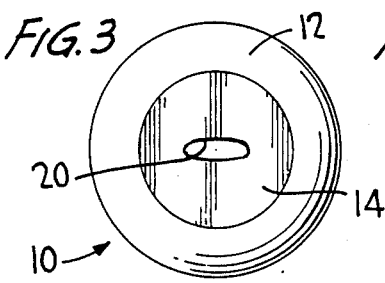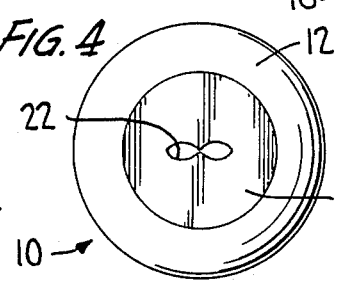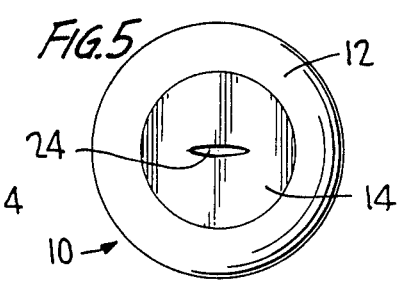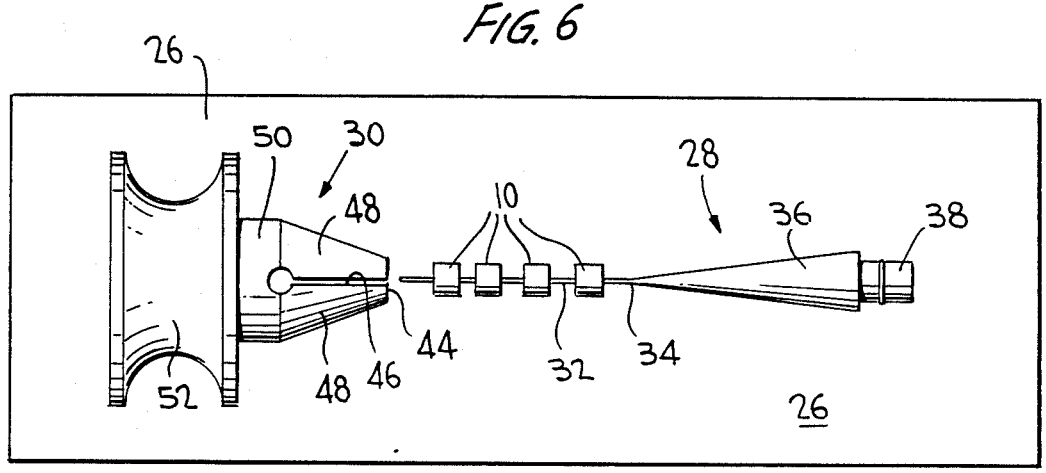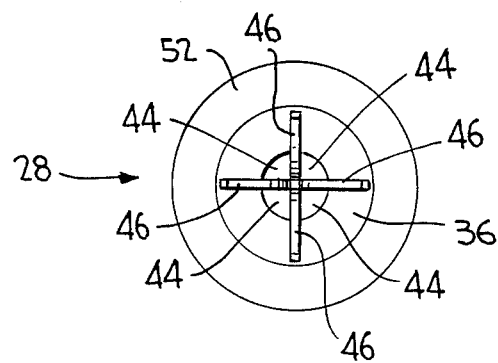

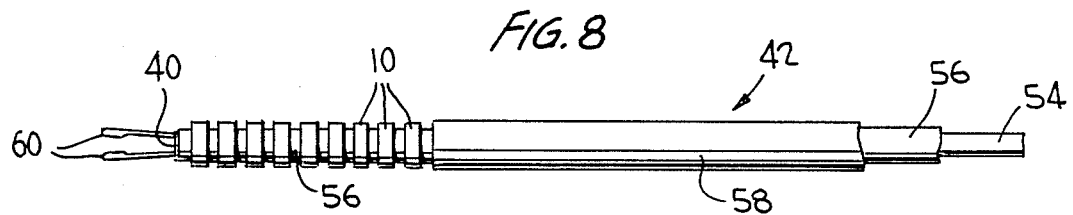
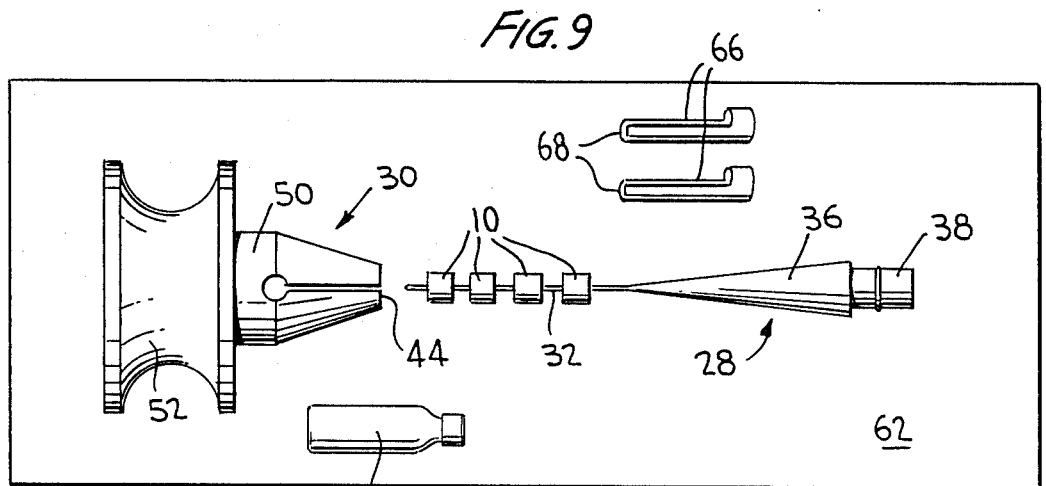
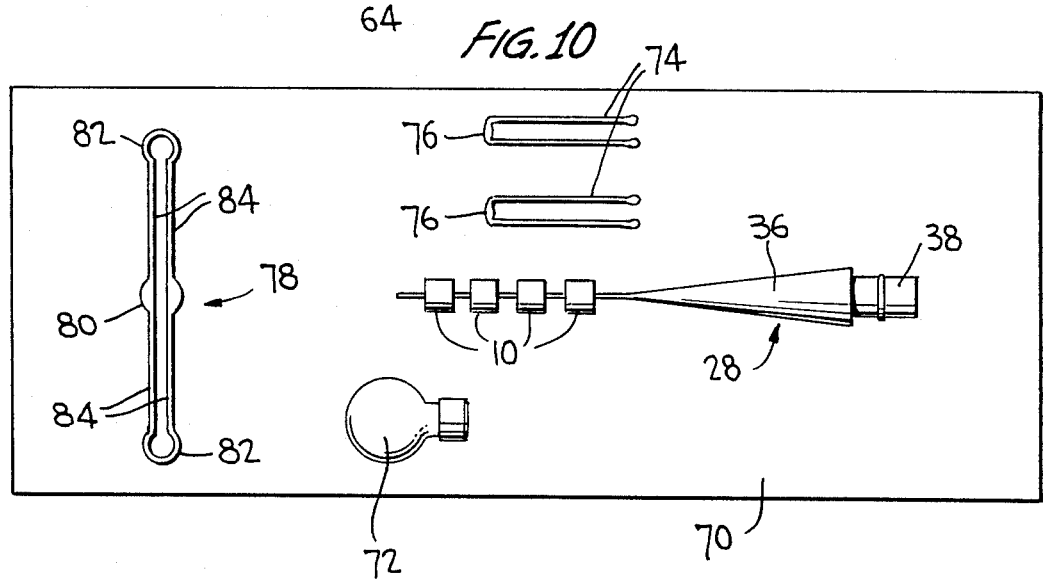

ELASTIC SURGICAL RING CLIP AND RING LOADER

CROSS REFERENCE TO RELATED APPLICATIONS

This application is a continuation-in-part of, makes reference to and incorporates herein, the disclosure of my earlier copending application entitled ELASTIC LIGATING RING CLIP filed on Oct. 21, 1985 and assigned Ser. No. 06/794,927 issued Jan. 3, 1989, which in turn is a divisional application which makes reference to and incorporates therein the disclosure of its copending application of ine entitled ELASTIC LIGATING RING CLIP filed on Apr. 20, 1982 and assigned Ser. No. 370,170, now U.S. Pat. No. 4,548,201, for purposes of claiming and obtaining the benefits provided by 35 U.S.C. ?120.

BACKGROUND OF THE INVENTION

This invention relates generally to surgical devices and, more particularly, to an improved elastic surgical ring clip and an improved ring loader for placing one or more elastic surgical rings onto the distal end of a ring applicator device. The elastic surgical ring clip is made of an elastic material and is configured so as to provide a clip having significantly increased, compressive or elastic strength. The ring loader includes a conically shaped ring expander onto which elastic surgical rings are loaded and a ring dilator having a plurality of fingers which engage the ring and push it up and over the ring expander and onto the distal end of a ring applicator device.

There are several prior art patents which disclose somewhat related elastic surgical clips and loading devices. The more relevant patents in the prior art include U.S. Pat. No. 4,167,188 issued to Coy L. Lay, deceased et al and my own prior U.S. Pat. No. 4,548,201. The Lay patent is directed to an elastic band designed and dimensioned for tying off human fallopian tubes or similar, anatomical tubular members. My prior patent shows an improved, elastic ligating ring clip and a ring loader for placing elastic rings onto the distal end of a ring applicator device including a conical ring expander and a ring dilator in the form of thin, flexible posts joined in pairs radiating from a deformable, elastic ring engaging aperture.

Nothing in the prior art discloses the surgical clip constructions of this invention which include an elastic body of a configuration which imparts greatly increased compressive or elastic strength to the elastic clip and a ring loader for placing one or more elastic surgical ring clips onto the distal end of a ring applicator device including a conical ring expander and a conical ring dilator having a plurality of fingers for pushing each ring along and over the expander and onto the distal end of a ring applicator device.

SUMMARY OF THE INVENTION

Accordingly, it is a principal object of this invention to provide a novel elastic surgical ring clip of elastic material which is configured to provide a clip having greatly increased, compressive strength.

It is another object of the invention to provide a new and improved elastic surgical ring clip having a lumen therethrough, the internal, cross-sectional configuration of the lumen being selected from a wide variety of shapes, such as elliptical, open figure eight and elongate slit to provide increased gripping power.

It is a further object of the invention to provide a ring loader for preparing a ring applicator device, the loader including a conical ring expander and a multi-legged, conical ring dilator for pushing an elastic ring up and over the conical ring expander and onto the distal end of a ring applicator device.

It is yet another object of the invention to provide a surgical clip and ring loader kit in package form having all parts necessary for a surgical procedure which minimizes the possibility of parts being lost or dropped during a surgical procedure.

BRIEF DESCRIPTION OF THE DRAWINGS

Further and more complete objects and advantages of the invention will become readily apparent by reference to the detailed specification and drawings in which:

FIG. 1 is a top plan view of one embodiment of the elastic surgical ring clip of this invention;

FIG. 2 is a side elevation view of the elastic surgical ring clip shown in FIG. 1;

FIG. 3 is a top plan view of another embodiment of the surgical ring clip of this invention;

FIG. 4 is a top plan view of yet another embodiment of the surgical ring clip of this invention;

FIG. 5 is a top plan view of yet a further embodiment of the elastic surgical ring clip of this invention;

FIG. 6 is a plan view of a kit including a plurality of elastic ring clips and a ring loader;

FIG. 7 is an end view of the ring dilator of this invention shown in the left hand portion of FIG. 6;

FIG. 8 is a partial, elevation view of a ring applicator device which may be used with this invention;

FIG. 9 is a plan view of a kit which includes the components of FIG. 6; and

FIG. 10 is a view similar to FIG. 9 and showing another kit.

DESCRIPTION OF THE PREFERRED EMBODIMENTS

Referring now to the drawings by reference character and, in particular, to FIGS. 1 and 2 thereof, an embodiment of the elastic surgical ring clip 10 is shown including a generally spherically configured body 12 made of a suitable elastic material. Preferably, body 12 is made of a suitable non-tissue reactive, medical grade, implantable, elastic material. For example, body 12 could be made of a silicone rubber known as Silastic. Other materials could be latex rubber or tetrafluoroethylene. Additionally, there are other known nonabsorbable elastic materials not harmful to anatomical tissue which could be used to make body 12. Furthermore, collagen or any other absorbable elastic materials might be used to make body 12.

Body 12 is configured to have a generally flattened top face 14 and a generally flattened bottom face 16. A tissue engaging lumen 18 is formed centrally through body 12 to enable tissue to be drawn into lumen 18 when it is expanded and, thereafter, the ring clip is allowed to return to its configuration shown in FIG. 1 thus to securely grasp and lock tissue therewithin.

The term "spherical" as used in this specification is meant to include any number of rounded shapes. The important point is that, in one embodiment, the clip may be greatly expanded at its equator about lumen 18 thus to provide a considerable amount of extra, elastic material in comparison to known, elastic surgical ring clips. This greater amount of elastic material imparts far more compressive strength to the clip 10 than is the case with known clips of this type.

As can be seen from FIG. 1, lumen 18 is generally cylindrical in configuration, or circular when viewed in cross-section. FIGS. 3, 4 and 5 disclose other lumen configurations. In FIG. 3 a generally elliptically shaped lumen 20 is shown. In FIG. 4, a lumen 22 is disclosed which is of double channel configuration, the channels being opened to each other and separated by inwardly extending nipples to form a sort of open, figure eight configuration in cross-section. In FIG. 5, the lumen 24 is of a generally slit configuration in cross-section, the slit shape being defined by a pair of facing, semicylindrical walls. It has been found that the lumen configurations in FIGS. 3, 4 and 5 can result in improved gripping of the tissue in the lumen as compared to the circular configuration shown in FIG. 1, regardless of the exterior shape of the ring clip.

Turning now to FIG. 6, a package or kit 26 is shown including a two-part ring loader. These components are an elastic ring expander 28 and a ring dilator 30. Expander 28 has an elongated, needle shaped elastic ring receiver 32 extended from its apex end 34 and onto which a plurality of elastic surgical ring clips are loaded, which may be the elastic rings 10 of this invention. The expander 28 is conically shaped as in indicated at 36 and terminates in a base 38 which is configured to be temporarily mounted on distal end 40 (FIG. 8) of a ring applicator device 42.

Ring dilator 30 is generally conically shaped. As is best seen in FIG. 7, the leading end of dilator 30 is flattened to form elastic ring engaging faces 44. The main body of dilator 30 is cross-slit as indicated at 46 to form four, expandable spring engaging fingers 48. These fingers 48 terminate in a base 50. Base 50 and fingers 48 may be of integral, one-piece construction as is illustrated. The fingers 48 are formed from a material which is elastic in nature and has sufficient elasticity so that the fingers may be spread apart when the device is used. Finally, dilator 30 includes a finger graspable means such as a spool shaped handle 52. This handle 52 greatly facilitates manipulation of dilator 30 in loading rings onto the expander 28.

The procedure for loading elastic ring clips such as clip 10 onto a ring applicator device 42 can now be explained. Device 42 includes telescopically interfitted members 54, 56 and 58. The distal end of inner member 54 may be provided with forceps 60. Member 54 is manipulated so that forceps 60 are withdrawn into distal end 40 of middle member 56. This is accomplished by moving inner member 54 in a proximal direction with respect to middle member 56, or to the right in the sense of FIG. 8. Thereafter, base 38 of expander 28 is inserted in distal end 40 of applicator device 42. Thereafter, receiver 32 is inserted centrally within dilator 30. Then handle 52 is grasped and pushed onto receiver 32. The rings 10 are then forced up the conical surface 36 of expander 28 and onto the member 56 of applicator device 42. The load, expanded rings are illustrated in FIG. 8.

Further details of construction and operation of ring applicator device 42 as well as the procedure for applying clips 10 to anatomical tissue are set forth in my copending application, Ser. No. filed May 14, 1987 049,503.

Referring now to FIG. 9, another embodiment of a kit 62 is shown. This kit is similar to kit 26 but further includes additional items such as a vial of anesthesia 64 and a pair of anatomical tissue engaging clips 66, each having a lumen 68 formed therethrough. Further details of clips 66 are found in my previously referenced copending patent application. In any event, these clips may be loaded onto the distal end 40 of a ring applicator device 42 in the manner just described above.

Yet another package or kit 70 is illustrated in FIG. 10. Conveniently, this package 70 might include a container 72 filled with lubricant. If desired, the package could also include the anesthesia vial 64. These items could also be included in the kit 26 illustrated in FIG. 6. Also, a pair of another type of surgical clips 74 could be provided, each having a central lumen 76. Further details of clips 74 are set forth in my previously referenced, copending patent application. Also, another form of a ring dilator 78 could be provided which has a central aperture 80, which is slipped onto receiver 32. Ring dilator 78 has spring ends 82, connected to aperture 80 by pairs of legs 84. Further details concerning structure and operation of dilator 78 are set forth in my prior U.S. Pat. No. 4, 548,201.

An expanded discussion of elastic ring clip 10 materials and uses of the clip follows. Clip 10 may be made of any non-tissue reactive, medical grade, absorbable or non-absorbable material which has elasticity, stretchability and full or substantially 100% elastic memory. Clip 10 should be able to return to its original size when released, even after being stretched to at least 5 times its original size for a period of time of at least 15 minutes. The lumen of clip 10 may have other configurations in a cross-section, such as triangular, square, rectangular, diamond, hexagonal, or octagonal. The interior surface of the lumen may be threaded or plain. Regardless of shape, the diameter of the lumen may be from 0.1 mm up to 15 mm. The outer diameter of the clip 10 may be in a range from 0.4 mm up to 18 mm and the height or length of clip 10 (from face 14 to face 16) can be in the range of from 0.25 mm up to 30 mm.

With further reference to the material from which clip 10 is made, it could be selected from any one of the following special medical grade families. These families include dimethylpolysaloxane, polyurethane, stainless steel, latex rubber, Teflon (polytetrafluoroethylene), or any other medical grade, stretchable material family so long as the material has substantially 100% elastic memory. In the event the material selected does not have the required elastic memory, the material could be coated or impregnated with a suitable medical grade material in order to render the clip useful.

The outer diameter of member 56 of the applicator device 42, onto which clips 10 are loaded, preferably should not be larger than 5 times the diameter of the lumen of the clip 10.

Clip 10 is implantable permanently on tissue organ structures, animal or human. It may be used as a ligature in such procedures as tubal ligation, vas ligation, blood vessel ligation and any organ structure strangulation procedure. Since clip 10 is ring-shaped, it can be used to ligate any anatomical tubular structure by being placed about a looped tubular structure. This is accomplished by manipulating forceps 60 to engage a tubular structure and then withdraw the structure within end 40 of applicator device 42 to create a loop in the tubular structure. Thereafter, a clip 10 is slipped over the looped tubular structure.

In summary, clip 10 is a permanent, implantable clip, made of either absorbable or non-absorbable material, and is useful in the following procedures: female tubal ligation, male vasectomy, bleeding vessel ligature, polypectomy, hemorrhoidectomy, uterine suspension (by shortening round ligaments), and any surgical blood vessel ligature procedures, human or animal.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

I claim:

1. An elastic surgical ring clip comprising:
   a body made of elastic material, said body having a generally spherical configuration exhibiting a pair of generally flattened and diametrically opposed faces, and
   means defining an anatomical tissue engaging lumen generally extending centrally through said elastic body with opposite ends of the lumen forming orifices centrally disposed in said opposed faces,
   said opposed faces having greatest cross-sectional dimensions in a plane perpendicular to a longitudinal axis of said lumen, substantially less than corresponding greatest cross-sectional dimensions of said spherical configuration of said body taken parallel to said plane,
   said body being made of an elastic material having sufficient elastic memory to return to its initial configuration after being stretched to enlarge said lumen so that tissue may be drawn into said lumen, whereby, upon return of said clip to its initial configuration with tissue located within said lumen, secure engagement of said clip about tissue is assured.

2. The surgical ring clip as claimed in claim 1 wherein said lumen is generally cylindrical in configuration.

3. The surgical ring clip as claimed in claim 1 wherein said lumen is generally elliptically configured in cross-section 4. The surgical ring clip as claimed in claim 1 wherein said lumen has a generally double channel configuration in cross-section with said channels being defined by inwardly extending nipples which can be separated to open the channels to each other thus to form a generally open figure eight lumen configuration in cross-section.

5. The surgical ring clip as claimed in claim 1 wherein said lumen is a generally narrow slit in cross-section.

6. The surgical ring clip as claimed in claim 1, further comprising in kit form a ring loader and a ring dilator for preparing a ring applicator device to apply one or more of said surgical ring clips, said ring loader comprising an elongate needle shaped receiver onto which one or more of said clips may be loaded by inserting the receiver through said clip lumen, a conically shaped ring clip expander having an apex and a base, said receiver extending from said apex and said base being configured to be temporarily mounted on the distal end of a ring applicator device, said ring dilator comprising a generally conically configured ring engaging portion and a base portion, said ring engaging portion being slit to define a plurality of ring engaging fingers for engaging an end of said elastic ring clip whereby one or more of said rings are advanced from said receiver, expanded by being pushed over said conical ring expander, and positioned on the distal end of a ring applicator by being pushed beyond said conical receiver base.

7. The surgical ring clip and ring loader, combination as claimed in claim 6 wherein said ring dilator base portion further comprises finger graspable means for facilitating a ring loading procedure.

8. The surgical ring clip and ring loader combination as claimed in claim 6 wherein said dilator ring engaging portion and base portion are of integral, one-piece construction and made of an elastic material whereby said fingers are spread apart as they are advanced over said conical expander.

9. A kit for preparing a ring applicator device to apply one or more elastic surgical rings onto anatomical tissue, comprising:
   a plurality of elastic surgical rings each having a substantially solid body made of elastic material, said body having a generally spherical configuration exhibiting a pair of generally flattened and diametrically opposed faces, and an anatomical tissue engaging lumen generally extending centrally through said elastic body with opposite ends of the lumen forming orifices centrally disposed in said opposed faces, said opposed faces having greatest cross-sectional dimensions in a plane perpendicular to a longitudinal axis of said lumen, substantially less than corresponding greatest cross-sectional dimensions of said spherical configuration of said body taken parallel to said plane, each of said bodies being made of an elastic material having sufifficient elastic memory to return to an initial configuration after beomg stretched to enlarge said lumen so that anatomical tissue may be drawn into said lumen, whereby, upon return of said clip to its initial configuration with anatomical tissue located within said lumen, secure engagement of said clip about anatomical tissue is assured,
   a ring loader having an elongate needle shaped receiver onto which one or more of said elastic surgical rings are loaded with the receiver inserted through the lumen,
   a conically shaped elastic ring expander having an apex and a base, said receiver extending from said apex and said base being configured to be temporarily mounted on the distal end of a ring applicator device, and
   a ring dilator having a generally conically configured ring engaging portion being slit to define a plurality of ring engaging fingers for engaging an end of one of said one or more elastic rings loaded onto said receiver whereby one or more elastic rings may be advanced from the receiver, expanded by being pushed over said conical ring expander, and positioned on the distal e or a ring applicator be being pushed beyond said conical receiver base.

10. The kit as claimed in claim 9 wherein said ring dilator base portion further comprises finger graspable means for facilitating a ring loading procedure.

11. The kit as claimed in claim 9 wherein said ring engaging portion and said base portion are of integral, one-piece construction and made of a shape retaining elastic material whereby said fingers are spread apart as they are advanced over said conical expander and return to their original configuration after removal of said dilator from said loader.

12. The kit of claim 9, further comprising a plurality of said elastic surgical ring clips, some on said receiver and some separate from said receiver.

13. An elastic surgical ring clip for engaging anatomical tissue, comprising:

a body made of elastic material; and means defining an anatomical tissue engaging lumen extending generally centrally through said elastic body, said body being made of an elastic mate having sufficient elastic memory to return to its initial configuration after being stretched to enlarge said lumen so that tissue may be drawn into said lumen, said lumen having generally an elliptical configuration in a cross-se taken in a plane perpendicular to a longitudinal axis of said lumen with major and minor axes of said elliptical configuration being perpendicular to said longitudinal axis with said major axis being greater in dimension than said minor axis.

14. The surgical ring clip of claim 13, wherein said lumen has a generally double channel configuration in cross-section with channels of said double channel configuration being defined by inwardly extending nipples which can be separated to open the channels to each other thus to form an open figure-eight lumen configuration in said cross-section.

15. The surgical ring clip of claim 13, wherein said lumen has a generally narrow slit configuration in said cross-section.

16. The surgical ring clip and ring loader combination as claimed in claim 6 wherein said ring engaging portion of said ring dilator has four ring engaging fingers.

17. The kit of claim 9 wherein said ring engaging portion of said ring dilator has four ring engaging fingers.

* * * * *